US008835691B2

(12) United States Patent
Klasovsky et al.

(10) Patent No.: US 8,835,691 B2
(45) Date of Patent: Sep. 16, 2014

(54) PROCESS FOR HOMOGENEOUSLY CATALYZED, HIGHLY SELECTIVE DIRECT AMINATION OF PRIMARY ALCOHOLS WITH AMMONIA TO PRIMARY AMINES WITH A HIGH VOLUME RATIO OF LIQUID PHASE TO GAS PHASE AND/OR HIGH PRESSURES

(75) Inventors: Florian Klasovsky, Haltern am See (DE); Jan Christoph Pfeffer, Hanau (DE); Thomas Tacke, Alzenau (DE); Thomas Haas, Muenster (DE); Matthias Beller, Nienhagen (DE); Angela Koeckritz, Berlin (DE); Jens Deutsch, Rangsdorf (DE); Andreas Martin, Berlin (DE); Sebastian Imm, Langenselbold (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 13/989,419

(22) PCT Filed: Dec. 7, 2011

(86) PCT No.: PCT/EP2011/071992
§ 371 (c)(1),
(2), (4) Date: May 24, 2013

(87) PCT Pub. No.: WO2012/076560
PCT Pub. Date: Jun. 14, 2012

(65) Prior Publication Data
US 2013/0245276 A1    Sep. 19, 2013

(30) Foreign Application Priority Data

Dec. 8, 2010   (DE) .................. 10 2010 062 645
Feb. 21, 2011  (DE) .................. 10 2011 004 470
May 3, 2011    (DE) .................. 10 2011 075 162

(51) Int. Cl.
C07C 209/00    (2006.01)
C07C 227/08    (2006.01)
C07C 231/12    (2006.01)
C07C 209/16    (2006.01)
C07D 213/38    (2006.01)
C07C 319/20    (2006.01)
C07D 307/52    (2006.01)
C07B 43/04     (2006.01)
C07C 213/02    (2006.01)

(52) U.S. Cl.
CPC .............. *C07B 43/04* (2013.01); *C07C 227/08* (2013.01); *C07C 231/12* (2013.01); *C07C 209/16* (2013.01); *C07D 213/38* (2013.01); *C07C 319/20* (2013.01); *C07D 307/52* (2013.01); *C07C 213/02* (2013.01)
USPC ....................................................... 564/480

(58) Field of Classification Search
USPC ....................................................... 564/480
See application file for complete search history.

(56) References Cited

U.S. PATENT DOCUMENTS

| 4,210,605 | A  | 7/1980  | Hoshino et al.      |
|-----------|----|---------|---------------------|
| 7,148,176 | B2 | 12/2006 | Beller et al.       |
| 7,758,897 | B2 | 7/2010  | Roettger et al.     |
| 8,372,595 | B2 | 2/2013  | Schaffer et al.     |
| 8,378,127 | B2 | 2/2013  | Dingerdissen et al. |
| 8,604,227 | B2 | 12/2013 | Petrat et al.       |
| 2001/0047097 | A1 | 11/2001 | Trauthwein et al. |
| 2002/0087036 | A1 | 7/2002  | Haas et al.       |
| 2003/0212298 | A1 | 11/2003 | Brasse et al.     |
| 2007/0207501 | A1 | 9/2007  | Wolf et al.       |
| 2010/0068773 | A1 | 3/2010  | Marx et al.       |
| 2010/0190224 | A1 | 7/2010  | Poetter et al.    |
| 2010/0261237 | A1 | 10/2010 | Verseck et al.    |
| 2010/0291644 | A1 | 11/2010 | Marx et al.       |
| 2010/0324257 | A1 | 12/2010 | Karau et al.      |
| 2011/0039313 | A1 | 2/2011  | Verseck et al.    |
| 2011/0039977 | A1 | 2/2011  | Schuetz et al.    |
| 2011/0118433 | A1 | 5/2011  | Pötter et al.     |
| 2011/0118504 | A1 | 5/2011  | Haas et al.       |
| 2011/0152525 | A1 | 6/2011  | Milstein et al.   |
| 2011/0171702 | A1 | 7/2011  | Reinecke et al.   |
| 2011/0189742 | A1 | 8/2011  | Haas et al.       |
| 2011/0251399 | A1 | 10/2011 | Dingerdissen et al. |
| 2011/0257429 | A1 | 10/2011 | Schraven et al.   |

(Continued)

FOREIGN PATENT DOCUMENTS

| WO | 2010 018570   |   | 2/2010 |           |
|----|---------------|---|--------|-----------|
| WO | WO2010018570  | * | 2/2010 | C07F 9/64 |

(Continued)

OTHER PUBLICATIONS

Hamid et al. Chem. Commun. 2007(7):725-727.*
Imm et al. Angew. Chem. Int. Ed. 2011, 50, 7599-7603.*
Dorwald F. A. Side Reactions in Organic Synthesis, 2005, Wiley: VCH, Weinheim p. IX of Preface p. 1-15.*
U.S. Appl. No. 09/424,701, filed Jan. 25, 2002, Beller, et al.
U.S. Appl. No. 14/000,400, filed Aug. 20, 2013, Klasovsky, et al.
U.S. Appl. No. 14/126,607, filed Dec. 16, 2013, Haas, et al.

(Continued)

*Primary Examiner* — Nizal Chandrakumar
(74) *Attorney, Agent, or Firm* — Oblon, Spivak, McClelland, Maier & Neustadt, L.L.P.

(57) ABSTRACT

The present invention relates to a process for preparing primary amines comprising the process steps
A) provision of a solution of a primary alcohol in a fluid, nongaseous phase,
B) contacting of the phase with free ammonia and/or at least one ammonia-releasing compound and a homogeneous catalyst and optionally
C) isolation of the primary amine formed in process step B),
characterized in that
the volume ratio of the volume of the liquid phase to the volume of the gas phase in process step B is greater than 0.05 and/or in that process step B is carried out at pressures greater than 10 bar.

16 Claims, No Drawings

(56) References Cited

U.S. PATENT DOCUMENTS

| | | |
|---|---|---|
| 2012/0034665 A1 | 2/2012 | Haas et al. |
| 2012/0041216 A1 | 2/2012 | Sieber et al. |
| 2012/0245375 A1 | 9/2012 | Hannen et al. |
| 2012/0264182 A1 | 10/2012 | Reinecke et al. |
| 2013/0052700 A1 | 2/2013 | Poetter et al. |
| 2013/0092233 A1 | 4/2013 | Pawlik et al. |
| 2013/0130319 A1 | 5/2013 | Schaffer et al. |
| 2013/0165672 A1 | 6/2013 | Klasovsky et al. |
| 2013/0165685 A1 | 6/2013 | Hannen et al. |
| 2013/0183725 A1 | 7/2013 | Poetter et al. |

FOREIGN PATENT DOCUMENTS

| | | |
|---|---|---|
| WO | 2010 089171 | 8/2010 |
| WO | 2012 031884 | 3/2012 |
| WO | 2012 113475 | 8/2012 |
| WO | 2012 171666 | 12/2012 |
| WO | 2013 020839 | 2/2013 |

OTHER PUBLICATIONS

Imm, S. et al., "An Efficient and General Synthesis of Primary Amines by Ruthenium-Catalyzed Amination of Secondary Alcohols with Ammonia", Communications, Angewandte Chemie, International Edition, vol. 49, No. 44, pp. 8126 to 8129 (2010), XP-002669003.

International Search Report Issued Feb. 24, 2012 in PCT/EP11/71992 Filed Dec. 7, 2011.

U.S. Appl. No. 14/237,121, filed Feb. 4, 2014, Haas, et al.
U.S. Appl. No. 14/233,505, filed Jan. 17, 2014, Poetter, et al.
U.S. Appl. No. 14/238,591, filed Feb. 12, 2014, Schaffer, et al.
U.S. Appl. No. 14/238,576, filed Feb. 12, 2014, Schaffer, et al.

\* cited by examiner

PROCESS FOR HOMOGENEOUSLY CATALYZED, HIGHLY SELECTIVE DIRECT AMINATION OF PRIMARY ALCOHOLS WITH AMMONIA TO PRIMARY AMINES WITH A HIGH VOLUME RATIO OF LIQUID PHASE TO GAS PHASE AND/OR HIGH PRESSURES

CROSS REFERENCE TO RELATED APPLICATIONS

The present application is a 35 U.S.C. §371 national stage patent application of International patent application PCT/EP2011/071992, filed on Dec. 7, 2011, published as WO/2012/076560 on Jun. 14, 2012, the text of which is incorporated by reference, and claims the benefit of the filing date of German application nos. 10 2010 062 645.7, filed on Dec. 8, 2010; 10 2011 004 470.1, filed on Feb. 21, 2011; and 10 2011 075 162.9, filed on May 3, 2011; the text of each of which is also incorporated by reference.

The present invention relates to a chemically catalysed liquid-phase process for the highly selective, direct single-stage amination of primary alcohols to form primary amines by means of ammonia using a homogeneous catalyst system at a high volume ratio of liquid phase to gas phase ($V_{liq}/V_{gas}$) and/or high pressures.

PRIOR ART

The conversion of oxygen-containing functional groups into nitrogen-containing functional groups is an essential transformation for the synthesis of many organic compounds. A series of classical methods for this purpose are known in the literature and in the industry.

In the overwhelming majority of publications, a primary or secondary alcohol is reacted with a primary or secondary organic amine. In contrast, the direct reaction of a primary or secondary alcohol with ammonia to form primary amines according to the reaction scheme shown has been described only for the use of particular process conditions, catalysts and only for a few alcohols.

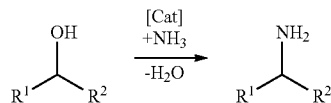

General Reaction Scheme for Obtaining Primary Amines from Primary or Secondary Alcohols The challenge facing all known processes is to achieve high selectivities to the primary amines since these are more nucleophilic than ammonia and can consequently react preferentially to form higher amines. While the conversion of an isolated hydroxyl function into an amino function proceeds approximately thermoneutrally, the formation of secondary and tertiary amines is exothermic with about 30 kJ/mol in each case and is therefore also thermodynamically favourable compared to the formation of primary amines.

Direct Amination in the Gas Phase

The single-stage direct transformation of a primary or secondary hydroxyl group into a primary amine with retention of the oxygen state of the carbon atom bearing the hydroxyl group by ammonia is in the case of lower, slightly volatile alcohols mainly restricted to gas-phase reactions. Here, the appropriate alcohol is vaporized and reacted under suitable conditions (pressure, temperature, hydrogen partial pressure and if applicable inert gas partial pressure) over a predominantly heterogeneous catalyst. This mode of operation is described, for example, in the publications U.S. Pat. No. 4,314,084, U.S. Pat. No. 5,530,127, U.S. Pat. No. 5,932,769, FR 1347648, U.S. Pat. No. 3,270,059, U.S. Pat. No. 4,111,840, U.S. Pat. No. 4,123,462, DE 1667193, Fischer et al. (J. Catal., 1999, 182, 289-291) or Jenzer et al. (Catal. Lett., 1999, 61, 111-114).

A disadvantage of most heterogeneously catalysed gas phase processes is the use of high temperatures (up to 400° C.) and pressures (up to 300 bar), as a consequence of which frequently considerable amounts of higher amines, alkenes and alkanes are formed in addition to the desired primary amines. In addition, due to the characteristic pressure and temperature conditions of a gas-phase reaction, only substrates which vaporize and can react without losses, or in the case of which the amines can be condensed or resublimed without losses, can be converted in economical yields into amines by means of the mentioned processes. Substrates or the corresponding amines thereof which are subject to decomposition under such conditions are therefore converted in liquid-phase syntheses in the literature and in industry.

Reductive Amination

Processes known to those skilled in the art for preparing primary amines from alcohols in the liquid phase by means of reductive amination utilize a multistage procedure which can be associated with a change in the oxidation state of the carbon atom bearing the hydroxyl group. With a change in the oxidation stage of the carbon atom bearing the hydroxyl group (reductive amination), alcohols can be conventionally prepared by oxidation into the corresponding carbonyl compound, followed by formation of the imine by reaction with an amine component (primary, secondary amine or ammonia) and subsequent homogeneously or heterogeneously catalysed reduction of the imine by means of hydrogen. However, the two-stage procedure with isolation of the carbonyl compound is time-consuming and costly.

Specific Multistage Processes

With retention of the oxygen state of the carbon atom bearing the hydroxyl group (direct amination), alcohols can be converted by means of multistage substitution reactions into amines. Disadvantages of such processes are not only the outlay for isolating the intermediates but also, in particular, the handling of explosive and toxic azides which are frequently used for this purpose.

An exception to the multistage mode of operation for the direct amination of alcohols with retention of the oxidation state of the carbon atom bearing the hydroxyl group is, for example, the sequential reaction of primary alcohols with dialkyl azodicarboxylates, bis-tert-butyl iminodicarbonate and immobilized triphenylphosphane, which according to Sun et al. (Tetrahedron Lett., 2007, 48, 7745-7746) allows, after addition of trifluoroacetic acid, a direct route to the primary amine without prior isolation of intermediates.

Fabiano et al. (Synlett, 1987, 1987, 190-192) use the toxic hydrazoic acid instead of bis-tert-butyl iminodicarbonate for the same purpose.

Direct Liquid-Phase Amination of Alcohols

The direct single-stage liquid-phase amination of optionally polyvalent primary alcohols by means of ammonia has been described for a relatively long time in the scientific and patent literature. In some cases, the processes described cannot be unambiguously classified as gas-phase or liquid-phase processes because of the process conditions employed.

According to DE 19507007, ethanolamine can be aminated over oxide-supported ruthenium catalysts at temperatures of about 170° C. and a pressure of 200 bar to form ethylenediamine, with the achievable yields remaining below 40%.

The preparation of monovalent, optionally functionalized primary amines in high yields from the corresponding monohydric, optionally functionalized primary alcohols is described in the studies of Gunanathan et al. (Angew. Chem. Int. Ed., 2008, 47, 8661-8664). Here, the direct single-stage amination of sometimes heteroatom-substituted primary aliphatic and benzylic alcohols by reaction with excess ammonia in a solvent at 7.5 bar and a reaction temperature of 135-180° C. for from 12 to 36 hours is described. The air-stable acridinyl-based pincer complex carbonylchlorohydrido[4,5-(di-i-propylphosphinomethylacridino)ruthenium (II)] is used as catalyst. However, it can be seen that aliphatic primary alcohols are increasingly less readily reacted in this process, especially in the absence of heteroatom substitutents and/or increasing proportions of linear carbon chains in the molecule. Thus, only low yields in the range from 54 to 82% are achieved in the case of alcohols which have at least one aliphatic alkyl radical containing at least three carbon atoms covalently bound to one another and no quaternary carbon atoms. It can therefore be assumed that none of the above-mentioned starting materials can be converted in high selectivity into the corresponding primary amine, since increased imine and secondary amine formation occurs.

Furthermore, WO 2010018570 describes the use of quinolinyl-based pincer ligands giving comparable yields, but likewise only in the case of short-chain substrates.

The direct single-stage liquid-phase amination of functionalized, optionally polyhydric alcohols by means of ammonia has been described over heterogeneous and homogeneous catalysts. The ether diol diethylene glycol was aminated in DE 3903367 by means of liquid ammonia at 200° C. over various zirconia dioxide-supported Cu—Co—Ni catalysts in a 30 bar hydrogen atmosphere. However, the reaction product is in no case the ether diamine, but instead only the downstream products aminoethoxyethanol and morpholine were isolated.

A decrease in the selectivity of the formation of primary amines with increasing chain length of the alcohol substrate is known in the literature for functionalized secondary alcohols. Thus, Imm et al. (S. Imm, S. Bähn, L. Neubert, H. Neumann, M. Beller, Angew. Chem. 2010, 122(44), 8303-6) describe a considerable decrease in the selectivity to the primary amine from 76 to 58% when 4-phenyl-2-butanol is aminated instead of 3-phenyl-2-propanol in the presence of homogeneous Ru catalysts. In an analogous way, a significantly lower amine yield (51.2%) is observed in the amination of aliphatic secondary alcohols in the case of 2-nonanol than in the case of the lower homologue 2-octanol (67.1%) (D. Pingen, C. Müller, D. Vogt, Angew. Chem. 2010, 122(44), 8307-10). It can therefore be assumed that higher and optionally additionally functionalized alcohols cannot be converted in high yields into the corresponding amines in this way.

According to DE 1570542, polyether diols such as polypropylene glycol can be converted directly into the corresponding diamines in high yields of up to 95.8% when the reaction is carried out at 240° C. in the presence of Raney nickel catalysts. However, this procedure is also unsuitable for the reaction of thermolabile substrates.

According to U.S. Pat. No. 4,153,581, the preparation of polyether amines can be carried out successfully using a Co—Cu—Zn catalyst, at as low as 140° C., but the presence of hydrogen is said to be absolutely necessary.

The examples mentioned illustrate by way of example the need for processes which achieve activation of, in particular, linear, aliphatic alcohols even without the stoichiometric use of difficult-to-obtain and toxic auxiliaries and also of hydrogen. In addition, a critical disadvantage of all processes which have hitherto been suitable for direct liquid-phase amination is that additional time-consuming and costly working steps have to be carried out to obtain and, if required, isolate and purify the intermediates occurring in the synthesis sequence.

According to the above-described prior art, there is no process known which describes the direct single-stage, hydrogen-free liquid-phase amination of primary alcohols, in particular those which have at least one aliphatic alkyl radical containing at least three carbon atoms covalently bound to one another and no quaternary carbon atoms, by means of ammonia to form primary amines in high yields under mild reaction conditions.

It was therefore an object of the present invention to provide a process for preparing primary amines from primary alcohols, in particular those which have at least one aliphatic alkyl radical containing at least three carbon atoms covalently bound to one another and no quaternary carbon atoms, which overcomes at least one of the disadvantages mentioned and can be carried out in an economically advantageous way.

DESCRIPTION OF THE INVENTION

We have now surprisingly found a process which allows the direct amination of primary alcohols, in particular those which have at least one aliphatic alkyl radical containing at least three carbon atoms covalently bound to one another and no quaternary carbon atoms, by means of ammonia in the presence of a homogeneous catalyst in high yields, with the primary hydroxyl group of the alcohol being aminated.

The present invention therefore provides a process which allows the direct, homogeneously catalysed liquid-phase amination of primary alcohols, in particular those which have at least one aliphatic alkyl radical containing at least three carbon atoms covalently bound to one another and no quaternary carbon atoms, in particular by means of a superstoichiometric amount of ammonia based on hydroxyl groups to be aminated, preferably in the absence of hydrogen, with the increase in selectivity being brought about by the use of a high processing pressure and/or, preferably and, a high volume ratio of liquid phase to gas phase.

An advantage of the process of the invention is that the isolation and purification of intermediates which is otherwise necessary in the reaction is avoided.

Another advantage is that the use of problematic auxiliaries such as azides can be avoided. An additional advantage is that the formation of coproducts does not occur as a result of the process of the invention and the formation of by-products can be reduced to a low level by appropriate choice of process conditions.

A further advantage is that the alcohol is reacted in the dissolved state.

Another advantage is that the amination of the alcohol can be effected without isolation and/or purification of intermediates.

The process of the invention for preparing primary amines comprises the process steps
A) provision of a solution of a primary alcohol in a fluid, nongaseous phase,
B) contacting of the phase with free ammonia and/or at least one ammonia-releasing compound and a homogeneous catalyst and optionally C) isolation of the primary amine formed in process step B), and is characterized in that the volume ratio of the volume of the liquid phase to the volume of the gas phase in process step B is greater than 0.05, preferably greater than 0.1, in particular greater than 0.2 and/or
in that process step B is carried out at pressures greater than 10 bar, preferably greater than 15 bar, in particular greater than 20 bar.

For the purposes of the present invention, the term "primary amine" likewise encompasses salts thereof and mixtures of the amine and/or salts thereof.

For the purposes of the present invention, the term "primary alcohol" refers to an organic compound which has at least one primary hydroxy group (R—CH$_2$(OH) where R=organic radical or H).

The term "quaternary carbon atom" refers to a carbon atom which has formed a covalent single bond to each of four carbon atoms.

Processes which are preferred according to the invention are characterized in that the volume ratio of the volume of the liquid phase to the volume of the gas phase in process step B is greater than 0.05, preferably greater than 0.1, in particular greater than 0.2, and
in that process step B is carried out at pressures greater than 10 bar, preferably greater than 15 bar, in particular greater than 20 bar; in particular, the volume ratio of the volume of the liquid phase to the volume of the gas phase in process step B is more than 0.2 and the pressure in process step B is greater than 20 bar.

According to the invention, the ammonia is preferably used in process step B) in a molar ratio based on the hydroxyl groups in the primary alcohol of at least 5:1, preferably 50:1, particularly preferably 500:1. The excess of ammonia leads to a rapid reaction and higher selectivity.

The alcohols used in the process of the invention can have further hydroxy groups in addition to the primary hydroxy group, so that a polyol having at least one primary hydroxy group is likewise a "primary alcohol" for the purposes of the present invention. In addition, the alcohols can have further heteroatoms in the molecule. Examples of such alcohols can be selected from the group consisting of aliphatic unbranched or branched alcohols (e.g. methanol, ethanol, 1-propanol, 1-butanol, 2-methyl-1-pentanol, . . . ) and benzylic alcohols (e.g. benzyl alcohol, furfuryl alcohol, nicotinyl alcohol, . . . ).

The process of the invention can likewise be advantageously used for primary alcohols which have a carboxy group or ester group, in particular a carboxy group.

It has surprisingly been found that under the reaction conditions using these substrates modification takes place preferentially only at the primary OH-group since the process is highly selective.

Preferred primary alcohols containing carboxy groups are, in particular, omega-hydroxy-carboxylic acids, in particular those derived from fatty acids. Examples of sources of such fatty acids can be the fractions of coconut oil, kernel oils or castor oil. Examples of such primary alcohols containing carboxy groups can be selected from the group consisting of 6-hydroxyhexanoic acid, 11-hydroxyundecanoic acid and 12-hydroxydodecanoic acid.

Preferred primary alcohols containing ester groups are, in particular, selected from the group consisting of the methyl esters, ethyl esters, n-propyl esters and isopropyl esters of the omega-hydroxycarboxylic acids, in particular those selected from the group consisting of methyl 6-hydroxyhexanoate, methyl 11-hydroxyundecanoate and methyl 12-hydroxydodecanoate.

Further alcohols which can preferably be used in the process of the invention have at least one aliphatic alkyl radical containing at least three carbon atoms covalenty bound to one another and no quaternary carbon atom.

In particular, the alcohols preferably do not contain any heteroatoms. In particular, alcohols which are characterized in that the aliphatic alkyl radical is a linear or branched alkyl radical containing at least 4, preferably at least 6, in particular at least 9, carbon atoms can also be used in the process of the invention. Particularly preferred alcohols encompass 1-butanol, 2-methyl-1-propanol, 1-pentanol, 3-methyl-1-butanol, 2-methyl-1-butanol, 1-hexanol, 4-methyl-1-pentanol, 3-methyl-1-pentanol, 2-methyl-1-pentanol, 2-ethyl-1-butanol, tripropylene glycol and the anhydrohexitols, in particular tripropylene glycol.

Illustrative alcohol concentrations used in the process of the invention are in the range from 0.1 to 10000 mmol/l, preferably from 0.1 to 1000 mmol/l and particularly preferably from 0.1 to 100 mmol/l, based on the fluid phase.

Possible homogeneous catalysts to be used in the process of the invention are all homogeneous catalysts known to those skilled in the art which are able to activate the CH bond of the carbon atom bearing the OH group to be aminated. Examples of such catalysts encompass alkali metal alkoxides, aluminum alkoxides and lanthanide alkoxides, inorganic compounds of noble metals (e.g. [RuCl$_3$*nH$_2$O], IrCl$_3$), monometallic or multimetallic, mononuclear or multinuclear coordination compounds of one or more noble metals selected from among the elements ruthenium (e.g. [RuCl$_2$(PPh$_3$)$_3$], [RuH$_2$(PPh$_3$)$_4$], the Shvo catalyst ([($\eta^4$-C$_4$Ph$_4$CO)Ru(CO)$_3$]$_2$), [Ru(cod)(cot)], [(PPh$_3$)$_2$Ru(CH$_3$CN)$_3$Cl]BPh$_4$, [Ru(p-cymene)Cl$_2$]$_2$, [Ru(p-cymene)Cl$_2$]$_2$/DPEphos, [Ru(PPh$_3$)$_3$(CO)H$_2$], [Ru$_3$(CO)$_{12}$], [Ru$_3$(CO)$_{12}$]/N-phenyl-2-(PCl$_2$)pyrrole, [RuCl$_2$(dmso)$_4$]), rhodium (e.g. the Wilkinson catalyst ([RhCl(PPh$_3$)$_3$]), [RhH(PPh$_3$)$_3$]), iridium (e.g. [IrCl$_3$(dmso)$_3$], [Cp*IrCl$_2$]$_2$, [Ir(cod)Cl]$_2$/(dppp)/Cs$_2$CO$_3$, [IrCl$_2$H(cod)]$_2$, KOH-activated phenanthroline-iridium complexes) and palladium ([Pd(PPh$_3$)$_4$], [PdCl$_2$(dppe)], [Pd(OAc)$_{2}$]) and the other platinum metals and iron.

Processes preferred according to the invention use compounds selected from the group consisting of carbonylchlorohydrido[4,5-(di-i-propylphosphinomethylacridino)ruthenium(II)], carbonylchlorohydrido[2-(dicyclohexylphosphino)-1-phenyl-1H-pyrryl)ruthenium (II)], carbonylchlorohydrido[2-(di-1-adamantylphosphino)-1-phenyl-1H-pyrryl)ruthenium(II)], carbonylchlorohydrido[2-(diisopropylphosphino)-1-phenyl-1H-pyrryl)ruthenium (II)] and ruthenium compounds having ligands of the CataCXium® P type as homogeneous catalysts.

In a further preferred embodiment of the process of the invention, catalysts which are known to those skilled in the art as catalysts for hydroformylation are used in step B). Transition metal carbonyl compounds of the general formula H$_x$M$_y$M'$_{y'}$(CO)$_z$L$_n$, where n=0 ("unmodified hydroformylation catalysts") or n≠0 ("modified hydroformylation catalysts") and x, y and z are integers, can be used for this purpose. y' can be zero when a monometallic catalyst is used, or y' can be a positive integer when a bimetallic catalyst is used. M and M' can be identical or different. As transition metals M and M', it is possible to use rhodium, cobalt, iridium, ruthenium, osmium, platinum, palladium, iron, nickel, chromium, molybdenum or manganese; preference is given to using rhodium, cobalt, iridium, ruthenium, osmium or platinum. The ligand L can be selected from the group consisting of phosphanes, phosphane oxides, phosphites, amines, amides, isonitriles, arsanes and stibanes; illustrative representatives are triphenylphosphane, triphenylphosphane oxide, triphenyiphosphanetrisulfonic acid sodium salt, triphenylamine an triphenylarsane. Illustrative hydroformylation catalysts are selected from the group consisting of HCo(CO)$_4$, HCo(CO)$_3$PBu$_3$, HRh(CO)(PR$_3$)$_3$, Rh$_4$(CO)$_{12}$, Rh$_6$(CO)$_{16}$, Rh$_2$(CO)$_4$Cl$_2$, CoRh(CO)$_7$, Co$_2$Rh$_2$(CO)$_{12}$, HRh(CO)$_3$.

A hydroformylation catalyst which is preferred in this context is a catalyst system containing at least one xantphos ligand of the general formula 1 and a transition metal compound.

The term "xantphos ligand" refers, for the purposes of the present invention, to a compound of the general formula 1,

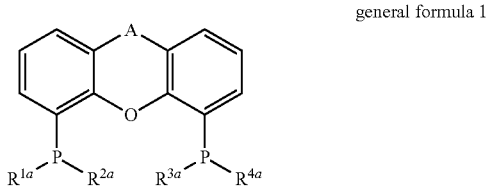

general formula 1 where $R^{1a}$, $R^{2a}$, $R^{3a}$ and $R^{4a}$ are identical or different and are selected independently from the group containing, preferably consisting of, phenyl, tert-butyl and isopropyl, and A is selected from the group containing, preferably consisting of —C(CH$_3$)$_2$—, —CH$_2$CH$_2$—, —Si(CH$_3$)$_2$—, —S—, —O—, —C(C(CH$_3$)$_2$)— and

Preference is given to using xantphos ligands in which $R^{1a}$=$R^{2a}$=$R^{3a}$=$R^{4a}$=phenyl and A=—C(CH$_3$)$_2$—.

In an alternative embodiment preference is given to using xantphos ligands in which $R^{1a}$=$R^{2a}$=$R^{3a}$=$R^{4a}$=phenyl and A=

(also known as DPEphos).

The transition metal is preferably selected from the group containing, preferably consisting of, ruthenium, cobalt, rhodium, iridium, nickel, palladium and platinum and the other platinum metals and iron. The transition metal is particularly preferably selected from the group consisting of ruthenium, iridium and palladium; particularly preferably from the group consisting of ruthenium and iridium, in particular ruthenium.

It may be mentioned that, depending on the selected combination of the catalyst-forming elements described, this catalyst can have an electric charge and be used in the form of a salt formed with the aid of appropriate counterions.

In a particularly preferred embodiment, the catalyst is the xanthene-based coordination compound carbonylchlorohydrido[9,9-dimethyl-4,5-bis(diphenylphosphino)xantheno]ruthenium(II):

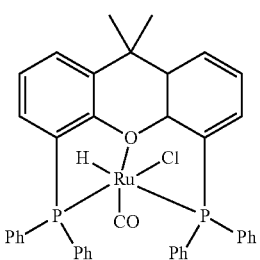

Carbonylchlorohydrido[9,9-dimethyl-4,5-bis(diphenylphosphino)xantheno]ruthenium(II)

It may be mentioned that, depending on the selected combination of the catalyst-forming elements described, this catalyst can have an electric charge and be used in the form of a salt formed with the aid of appropriate counterions.

The fluid phase used in process step A) can be formed by a solvent or a gas present in liquefied or supercritical form under the process conditions, in particular ammonia, or mixtures of the components mentioned.

As solvent, it is possible in this context to use water or organic solvent or mixtures thereof; these mixtures can be a homogeneous solution or else an emulsion. Particular preference is given to using at least one organic solvent. A selection, which is not to be construed as a limitation, of suitable organic solvents encompasses benzene, toluene, the xylene isomers, mesitylene, dioxane, THF, dimethoxyethane, anisole, cyclohexane and tert-butyl alcohol.

For the purposes of the present invention, the ammonia or ammonia-releasing compound used in process step B) includes, in particular, liquid or supercritical ammonia and/or a solution of ammonium salts in a solvent (e.g. ammonium hydroxide in water).

Preference is given to using gaseous or liquefied ammonia as free ammonia in process step B).

Process step B) is carried out at superatmospheric pressure. Illustrative pressures in process step B) of the process of the invention are in the range from 20 to 1000 bar, preferably from 20 to 500 bar, and particularly preferably from 20 to 100 bar. The pressure can be built up by injection of ammonia and/or a further gas, in particular an inert gas such as nitrogen or argon, with pressure buildup by means of gas mixtures of the two being preferred.

The temperatures in process step B) of the process of the invention are in a range which restricts decomposition reactions of primary alcohol, primary amine and all further intermediates occurring during the process leading to formation of by-products as a result of thermal stress to a minimum. For example, the temperatures are in the range from 80 to 220° C., preferably from 90 to 200° C. and particularly preferably from 100 to 170° C., measured in the fluid phase.

According to the invention, the process is preferably carried out in the absence of hydrogen, where "absence of hydrogen" means that no hydrogen is additionally introduced into the reaction; any traces of hydrogen present in the air are not taken into account in determining "absence of hydrogen" for the purposes of the present invention.

EXAMPLES

Example 1

Direct Single-Stage Amination of 1-hexanol by Means of Ammonia Over a Homogeneous Ruthenium Catalyst at a Low $V_{liq}/V_{gas}$ (Comparative Example, not According to the Invention, $V_{liq}/V_{gas}$=0.05)

Under an argon atmosphere, 1.022 g (10 mmol) of 1-hexanol, 0.006 g (0.01 mmol) of carbonylchlorohydrido[4,5-(di-i-propylphosphinomethylacridino)ruthenium(II)] as catalyst, 1 ml of water and 2 ml of dioxane as solvent were placed in a 90 ml Fischer-Porter reactor. The vessel was closed and pressurized with 20 bar of argon and depressurized three times. Ammonia was then introduced into the autoclave up to a pressure of 7.5 bar (overall $V_{liq}/V_{gas}$=0.05), the reactor was heated to 135° C. and maintained at this temperature for 30 hours. After cooling to room temperature, the reactor was opened and the reaction product was analysed by gas chromatography. 1-Hexylamine is obtained with a yield of 79.7% (99% conversion).

Example 2

Direct Single-Stage Amination of Furfuryl Alcohol by Means of Ammonia Over a Homogeneous Ruthenium Catalyst at a Low $V_{liq}V_{gas}$ ((Comparative Example, not According to the Invention, $V_{liq}V_{gas}$=0.05)

Under an argon atmosphere, 0.098 g (1 mmol) of furfuryl alcohol, 0.0128 g (0.02 mmol) of dodecacarbonyltriruthenium and 0.0204 g (0.06 mmol) of 2-(dicyclohexylphosphanyl)-1-phenyl-1-H-pyrrol as catalyst and 1 ml of 2-methyl-2-butanol as solvent were placed in a 50 ml steel tube. The vessel was closed and pressurized with 20 bar of argon and depressurized three times. The vessel was then cooled by means of dry ice and 0.6 g (1 ml, 35.3 mmol) of ammonia was condensed in (overall $V_{liq}/V_{gas}$=0.05), the reactor was heated to 150° C. and maintained at this temperature for 20 hours. After cooling to room temperature, the reactor was opened, the solvent was removed on a rotary evaporator and the residue was dissolved in methanol and analysed by gas chromatography. Furfurylamine is obtained in a yield of 71% (99% conversion).

Example 3

Direct Single-Stage Amination of Tripropylene Glycol by Means of Ammonia Over a Homogeneous Ruthenium Catalyst at High Pressure and a High $V_{liq}V_{gas}$ (According to the Invention, $V_{liq}V_{gas}$=0.3)

Under an argon atmosphere, 0.961 g (5 mmol) of tripropylene glycol, 0.0305 g (0.05 mmol) of carbonylchlorohydrido [4,5-(di-i-propylphosphinomethylacridino)ruthenium(II)] as catalyst and 25 ml of 2-methyl-2-butanol as solvent were placed in the glass liner of a 100 ml Hastelloy autoclave. The autoclave was closed, pressurized with 20 bar of argon and depressurized three times and again pressurized with 15 bar of argon. 2 g (2.95 ml; 117 mmol) of liquid ammonia were then introduced into the autoclave (overall $V_{liq}/V_{gas}$=0.3). The reaction mixture was stirred (600 rpm) at room temperature for 10 minutes, subsequently heated to an internal temperature of 170° C. while stirring and maintained at this temperature for 48 hours, with a pressure of 45 bar being established. After cooling to room temperature, careful depressurization of the reaction mixture and pressurization with 20 bar of argon and subsequent depressurization three times, the autoclave was opened, the reaction mixture was filtered through kieselguhr and the filtrate was evaporated under reduced pressure on a rotary evaporator to remove the solvent. The crude product obtained was purified by bulb tube distillation under reduced pressure. This gave the diamine of tripropylene glycol in a yield of 91% of theory, boiling range 90-95° C. air bath temperature at 10 mbar.

Example 4

Direct Single-Stage Amination of 1-hexanol (Alcohol) by Means of Ammonia Over a Homogeneous Ruthenium Catalyst (Variation of Pressure and $V_{liq}V_{gas}$)

Under an argon atmosphere, $m_H$ g of 1-hexanol, $m_{Ru}$ g of [carbonylchlorohydrido-tris(triphenylphosphane)ruthenium (II)] and $m_P$ g of 9,9-dimethyl-4,5-bis(diphenylphosphino)xanthene as catalyst and $V_{LM}$ ml of 2-methyl-2-butanol as solvent were placed in a 50 ml steel tube. The vessel was closed and pressurized with 20 bar of argon and depressurized three times. The vessel was then cooled by means of dry ice and $m_A$ g of ammonia was condensed in. After pressurization to a differential pressure of a further p bar of argon, the reactor was heated to 130° C. and maintained at this temperature for 20 hours. After cooling to room temperature, the reactor was depressurized and opened, the solvent is removed on a rotary evaporator and the residue is dissolved in methanol and analysed by gas chromatography. Reaction parameters and also conversions and selectivities to the desired reaction product 1-hexylamine are shown in the following table. The results show that the selectivity to the target product can be increased both by increasing the ratio $V_{liq}/V_{gas}$ and by increasing the pressure and also by simultaneously increasing both parameters.

| No. | according to the invention | $m_H$ [g][1] | $m_{Ru}$ [g][2] | $m_P$ [g][3] | $V_{LM}$ [ml][4] | $m_A$ [g][5] | p [bar][6] | $V_{liq}/V_{gas}$ [—][7] | Conv. [%][8] | S [%][9] |
|---|---|---|---|---|---|---|---|---|---|---|
| 4.1 | − | 0.10 | 0.029 | 0.017 | 1 | 0.3 | 0 | 0.03 | 100 | 31 |
| 4.2 | + | 0.10 | 0.029 | 0.017 | 1 | 0.3 | 20 | 0.03 | 100 | 37 |
| 4.3 | + | 0.41 | 0.116 | 0.069 | 4 | 1.2 | 0 | 0.14 | 80 | 50 |
| 4.4 | + | 0.41 | 0.116 | 0.069 | 4 | 1.2 | 20 | 0.14 | 65 | 48 |

[1]Mass of 1-hexanol;
[2]Mass of [carbonylchlorohydridotris(triphenylphosphane)ruthenium(II)];
[3]Mass of xantphos;
[4]Volume of solvent;
[5]Mass of ammonia;
[6]pressure established under reaction conditions;
[7]Ratio of liquid phase volume to gas phase volume;
[8]Conversion of 1-hexanol;
[9]Selectivity to 1-hexylamine.

Example 5

Direct Single-Stage Amination of Methyl 12-hydroxydodecanoate (Hydroxy Acid) by Means of Ammonia Over a Homogeneous Ruthenium Catalyst (Variation of Pressure and $V_{liq}/V_{gas}$)

Under an argon atmosphere, $m_H$ g of methyl 12-hydroxydodecanoate, $m_{Ru}$ g of [carbonylchlorohydridotris(triphenylphosphane)ruthenium(II)] and $m_P$ g of 9,9-dimethyl-4,5-bis(diphenylphosphino)xanthene as catalyst and $V_{LM}$ ml of 2-methyl-2-butanol as solvent were placed in a 50 ml steel tube. The vessel was closed and pressurized with 20 bar of argon and depressurized three times. The vessel was then cooled by means of dry ice and $m_A$ g of ammonia was condensed in. After pressurization to a differential pressure of a further p bar of argon, the reactor was heated to 130° C. and maintained at this temperature for 20 hours. After cooling to room temperature, the reactor was depressurized and opened, the solvent is removed on a rotary evaporator and the residue is dissolved in methanol and analysed by gas chromatography. Reaction parameters and also conversions and selectivities to the desired reaction product methyl 12-aminododecanoate are shown in the following table. The results show that the selectivity to the target product can be increased both by increasing the ratio $V_{liq}/V_{gas}$ and by increasing the pressure and also by simultaneously increasing both parameters.

closed and pressurized with 20 bar of argon and depressurized three times. The vessel was then cooled by means of dry ice and $m_A$ g of ammonia was condensed in. The reactor was heated to T° C. and maintained at this temperature for 20 hours. After cooling to room temperature, the reactor was depressurized and opened, the solvent is removed on a rotary evaporator and the residue is dissolved in methanol and analysed by gas chromatography. Reaction parameters and also conversions and selectivities to the desired reaction products are shown in the following table. The results show that many different hydroxy-functionalized substrates can be aminated using the method described.

| No. | according to the invention | $m_H$ [g][1] | $m_{Ru}$ [g][2] | $m_P$ [g][3] | $V_{LM}$ [ml][4] | $m_A$ [g][5] | p [bar][6] | $V_{liq}/V_{gas}$ [—][7] | Conv. [%][8] | S [%][9] |
|---|---|---|---|---|---|---|---|---|---|---|
| 5.1 | − | 0.23 | 0.029 | 0.017 | 1 | 0.3 | 0 | 0.04 | 100 | 30 |
| 5.2 | + | 0.23 | 0.029 | 0.017 | 1 | 0.3 | 20 | 0.04 | 98 | 42 |
| 5.3 | + | 0.92 | 0.116 | 0.069 | 4 | 1.2 | 0 | 0.16 | 96 | 50 |
| 5.4 | + | 0.92 | 0.116 | 0.069 | 4 | 1.2 | 20 | 0.16 | 77 | 61 |

[1] Mass of methyl 12-hydroxydodecanoate;
[2] Mass of [carbonylchlorohydridotris(triphenyl-phosphane)ruthenium(II)];
[3] Mass of xantphos;
[4] Volume of solvent;
[5] Mass of ammonia;
[6] pressure established under reaction conditions;
[7] Ratio of liquid phase volume to gas phase volume;
[8] Conversion of methyl 12-hydroxydodecanoate;
[9] Selectivity to methyl 12-aminododecanoate.

Example 6

Direct Single-Stage Amination of Alcohols and Hydroxy Acids by Means of Ammonia Over a Homogeneous Ruthenium Catalyst and Xantphos at a High $V_{liq}/V_{gas}$ (According to the Invention)

Under an argon atmosphere, $m_E$ g of starting material, $m_{Ru}$ g of [carbonylchlorohydrido-tris(triphenylphosphane)ruthenium(II)] and $m_P$ g of 9,9-dimethyl-4,5-bis(diphenylphosphino)xanthene as catalyst and $V_{LM}$ ml of 2-methyl-2-butanol as solvent were placed in a 50 ml steel tube. The vessel was

| Starting material | $m_E$ [g][1] | $m_{Ru}$ [g][2] | $m_P$ [g][3] | $V_{LM}$ [ml][4] | $m_A$ [g][5] | T [° C.][6] | $V_{liq}/V_{gas}$ [—][7] | Conv. [%][8] | S [%][9] |
|---|---|---|---|---|---|---|---|---|---|
| Tetraethylene glycol | 0.19 | 0.029 | 0.017 | 1 | 1 | 140 | 0.06 | 100 | 97 |
| p-hydroxymethylbenzyl alcohol | 0.14 | 0.029 | 0.017 | 3 | 1 | 150 | 0.10 | 100 | 48 |
| p-hydroxymethylbenzyl alcohol | 0.14 | 0.029 | 0.017 | 5 | 1 | 150 | 0.15 | 100 | 76 |
| m-hydroxymethylbenzyl alcohol | 0.14 | 0.029 | 0.017 | 5 | 1 | 150 | 0.15 | 100 | 70 |
| 1-octanol | 0.13 | 0.029 | 0.017 | 1 | 1 | 130 | 0.06 | 99 | 53 |
| 1-octanol | 0.13 | 0.029 | 0.017 | 3 | 1 | 130 | 0.10 | 80 | 79 |
| 1-octanol | 0.13 | 0.029 | 0.017 | 3 | 1 | 140 | 0.10 | 99 | 80 |
| 2-phenylethanol | 0.12 | 0.029 | 0.017 | 3 | 1 | 140 | 0.10 | 99 | 94 |
| Benzyl alcohol | 0.11 | 0.029 | 0.017 | 3 | 1 | 140 | 0.10 | 100 | 87 |
| 3-pyridinylmethanol | 0.11 | 0.029 | 0.017 | 3 | 1 | 140 | 0.10 | 100 | 96 |
| Methyl 10-hydroxydecanoate | 0.20 | 0.029 | 0.017 | 3 | 1 | 130 | 0.10 | 100 | 75 |
| Methyl 4-hydroxymethylbenzoate | 0.17 | 0.029 | 0.017 | 3 | 0.6 | 130 | 0.09 | 100 | 92 |

[1] Mass of educt;
[2] Mass of [carbonylchlorohydridotris-(triphenylphosphane)ruthenium(II)];
[3] Mass of xantphos;
[4] Volume of solvent;
[5] Mass of ammonia;
[6] Reaction temperature;
[7] Ratio of liquid phase volume to gas phase volume;
[8] Conversion of educt;
[9] Selectivity to product.

Example 7

Direct Single-Stage Amination of Glycolic Acid and Anilidoglycolic Acid by Means of Ammonia Over a Homogeneous Ruthenium Catalyst and Xantphos (Variation of $V_{liq}/V_{gas}$)

Under an argon atmosphere, $m_E$ g of starting material, $m_{Ru}$ g of [carbonylchlorohydrido-tris(triphenylphosphane)ruthenium(II)] and $m_P$ g of 9,9-dimethyl-4,5-bis(diphenylphosphino)xanthene as catalyst and $V_{LM}$ ml of 2-methyl-2-butanol as solvent were placed in a 50 ml steel tube. The vessel was closed and pressurized with 20 bar of argon and depressurized three times. The vessel was then cooled by means of dry ice and $m_A$ g of ammonia was condensed in. The reactor was heated to T° C. and maintained at this temperature for 20 hours. After cooling to room temperature, the reactor was depressurized and opened, the solvent is removed on a rotary evaporator and the residue is dissolved in methanol and analysed by gas chromatography. Reaction parameters and also conversions and selectivities to the desired reaction products are shown in the following table. The results show that in the case of both substrates an increase in the selectivity to the desired product can be achieved by increasing the ratio $V_{liq}/V_{gas}$.

| Starting material | $m_E$ [g][1] | $m_{Ru}$ [g][2] | $m_P$ [g][3] | $V_{LM}$ [ml][4] | $m_A$ [g][5] | $V_{liq}/V_{gas}$ [—][6] | Conv. [%][7] | S [%][8] |
|---|---|---|---|---|---|---|---|---|
| Glycolic acid | 0.076 | 0.029 | 0.017 | 1 | 0.3 | 0.03 | 80 | 10 |
| Glycolic acid | 0.304 | 0.116 | 0.069 | 4 | 1.2 | 0.14 | 74 | 24 |
| Anilidoglycolic acid | 0.151 | 0.029 | 0.017 | 1 | 0.3 | 0.03 | 55 | 29 |
| Anilidoglycolic acid | 0.605 | 0.116 | 0.069 | 4 | 1.2 | 0.14 | 47 | 38 |

[1] Mass of starting material;
[2] Mass of [carbonylchlorohydridotris(triphenylphosphane)ruthenium(II)];
[3] Mass of xantphos;
[4] Volume of solvent;
[5] Mass of ammonia;
[6] Ratio of liquid phase volume to gas phase volume;
[7] Conversion of starting material;
[8] Selectivity to primary aminoglycolic acid (derivative).

Example 8

Direct Single-Stage Amination of 2-methylthioethanol by Means of Ammonia Over a Homogeneous Ruthenium Catalyst and Xantphos (Variation of $V_{liq}/V_{gas}$)

Under an argon atmosphere, $m_M$ g of 2-methylthioethanol, $m_{Ru}$ g of [carbonylchlorohydridotris(triphenylphosphane)ruthenium(II)] as catalyst, $m_P$ g of xantphos and $V_{LM}$ ml of 2-methyl-2-butanol as solvent are placed in the glass liner of a 314 ml Hastelloy autoclave. The autoclave is closed, pressurized with 5 bar of nitrogen, depressurized and cooled to −70° C. $m_A$ g of liquid ammonia are then condensed into the autoclave. The reaction mixture is subsequently stirred (600 rpm) at room temperature for 10 minutes, then heated to an internal temperature of 170° C. while stirring and maintained at this temperature for 48 hours. After cooling to room temperature, careful depressurization of the mixture and pressurization with 5 bar of nitrogen with subsequent depressurization, the autoclave is opened and the reaction mixture is analysed by means of a gas chromatograph. Reaction parameters and also conversions and selectivities to the desired primary amine 2-methylthioethylamine are shown in the following table. The results show that the selectivity to the target product can be increased by increasing the ratio $V_{liq}/V_{gas}$.

| No. | $m_O$ [g][1] | $m_{Ru}$ [g][2] | $m_P$ [g][3] | $V_{LM}$ [ml][4] | $m_A$ [g][5] | $V_{liq}/V_{gas}$ [—][6] | U [%][7] | S [%][8] |
|---|---|---|---|---|---|---|---|---|
| 1 | 2.3 | 0.7 | 0.42 | 24.6 | 9.8 | 0.14 | 89 | 42 |
| 2 | 11.7 | 3.57 | 2.18 | 125.2 | 37.5 | 1.68 | 78 | 43 |

[1] Mass of 2-methylthioethanol;
[2] Mass of [carbonylchlorohydridotris(triphenylphosphane)ruthenium(II)];
[3] Mass of xantphos;
[4] Volume of solvent;
[5] Mass of ammonia;
[6] Ratio of liquid phase volume to gas phase volume;
[7] Conversion of 2-methylthioethanol;
[8] Selectivity to 2-methylthioethylamine.

The invention claimed is:

1. A process for preparing a primary amine, the process comprising
   A) contacting (i) a solution of a primary alcohol in a fluid, nongaseous phase with (ii) free ammonia or an ammonia-releasing compound and (iii) a homogeneous ruthenium comprising catalyst, to form a primary amine, and optionally
   B) isolating the primary amine,
   wherein a volume ratio of a volume of a liquid phase to a volume of a gas phase in the contacting is greater than 0.10 and requiring and the contacting is performed at a pressure range from 20 to 100 bar.

2. The process of claim 1, wherein in the contacting the ammonia is present in a molar ratio based on hydroxyl groups in the primary alcohol of at least 5:1.

3. The process of claim 1, wherein the primary alcohol comprises a carboxyl or ester group.

4. The process of claim 1, wherein the primary alcohol comprises an aliphatic alkyl radical comprising at least three carbon atoms covalently bound to one another and no quaternary carbon atom.

5. The process of claim 1, wherein the primary alcohol comprises no heteroatoms.

6. The process of claim 4, wherein the aliphatic alkyl radical is a linear or branched alkyl radical comprising at least 4 carbon atoms.

7. The process of claim 1, wherein the primary alcohol is selected from the group consisting of 1-butanol, 2-methyl-1-propanol, 1-pentanol, 3-methyl-1-butanol, 2-methyl-1-butanol, 1-hexanol, 4-methyl-1-pentanol, 3-methyl-1-pentanol, 2-methyl-1-pentanol, 2-ethyl-1-butanol, tripropylene glycol, an anhydrohexitol, and tripropylene glycol.

8. The process of claim 1, wherein a concentration of the primary alcohol in (i) is from 0.1 to 10000 mmol/l.

9. The process of claim 1, wherein (ii) comprises at least one selected from the group consisting of liquid ammonia, supercritical ammonia, and a solution of at least one ammonium salt in a solvent.

10. The process of claim 1, wherein the contacting is performed
    in a temperature range from 80 to 220° C.

11. The process of claim 1, performed in the absence of hydrogen.

12. The process of claim 1, comprising B) isolating the primary amine.

13. The process of claim 1, wherein in the contacting the ammonia is present in a molar ratio based on hydroxyl groups in the primary alcohol of at least 50:1.

14. The process of claim 1, wherein in the contacting the ammonia is present in a molar ratio based on hydroxyl groups in the primary alcohol of at least 500:1.

15. The process of claim 4, wherein the aliphatic alkyl radical is a linear or branched alkyl radical comprising at least 6 carbon atoms.

16. The process of claim 4, wherein the aliphatic alkyl radical is a linear or branched alkyl radical comprising at least 9 carbon atoms.

* * * * *